US00PP35583P2

(12) United States Plant Patent
Bernuetz

(10) Patent No.: US PP35,583 P2
(45) Date of Patent: Jan. 16, 2024

(54) ***EUPHORBIA* PLANT NAMED 'BONPRI 1756'**

(50) Latin Name: ***Euphorbia pulcherrima* Willd. ex Klotzsch X *Euphorbia cornastra***
Varietal Denomination: BONPRI 1756

(71) Applicant: Andrew Bernuetz, Mulgoa (AU)

(72) Inventor: Andrew Bernuetz, Mulgoa (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/126,385

(22) Filed: Mar. 25, 2023

(51) Int. Cl.
*A01H 5/12* (2018.01)
*A01H 6/38* (2018.01)

(52) U.S. Cl.
USPC ..... Plt./307

(58) Field of Classification Search
USPC ..... Plt./302, 303, 307
See application file for complete search history.

(56) References Cited

PUBLICATIONS

CPVO Register-S2/S3; CPVO Application Consultation, version 4.10.7 (retrieved from the Internet on Jul. 28, 2023 at https://online.plantvarieties.eu/publicSearch); citation for 'Bonpri 1756'.*

* cited by examiner

*Primary Examiner* — Susan McCormick Ewoldt
(74) *Attorney, Agent, or Firm* — C. Anne Whealy

(57) ABSTRACT

A new and distinct cultivar of *Euphorbia* plant named 'BONPRI 1756', characterized by its upright and mounded plant habit; vigorous growth habit; freely branching habit; inflorescences with red-colored flower bracts; and good post-production longevity.

1 Drawing Sheet

Figure 1:
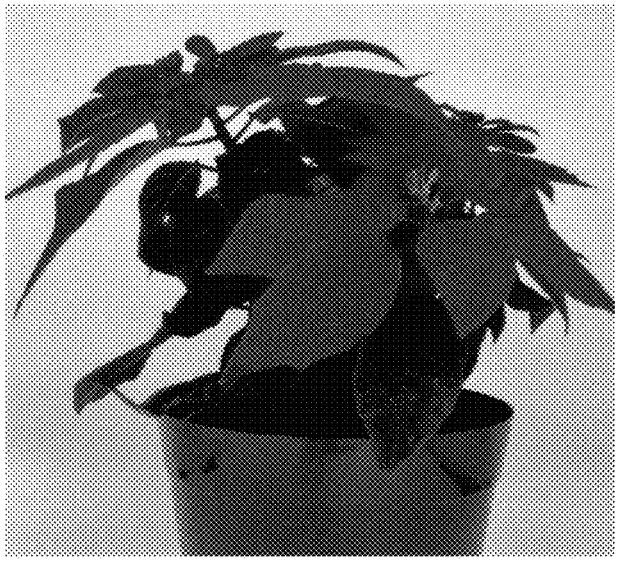

Botanical designation: *Euphorbia pulcherrima* Willd. ex Klotzsch X *Euphorbia cornastra.*
Cultivar denomination: 'BONPRI 1756'.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'BONPRI 1756'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number Eu 15-16, not patented. The new *Euphorbia* plant was discovered and selected by the Inventor as a single flowering plant from within a population of plants of the mutation parent selection in a controlled greenhouse environment in Yellow Rock, New South Wales, Australia in September, 2017.

Asexual reproduction of the new *Euphorbia* plant by terminal vegetative cuttings in a controlled greenhouse environment in Yellow Rock, New South Wales, Australia since September, 2017 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BONPRI 1756'. These characteristics in combination distinguish 'BONPRI 1756' as a new and distinct *Euphorbia* plant:

1. Upright and mounded plant habit.
2. Vigorous growth habit.
3. Freely branching habit.
4. Inflorescences with red-colored flower bracts.
5. Good post-production longevity.

Plants of the new *Euphorbia* differ primarily from plants of the mutation parent selection in flower bract color as flower bracts of plants of the new *Euphorbia* are more orangish red in color than flower bracts of plants of the mutation parent selection.

Plants of the new *Euphorbia* can be compared to plants of the *Euphorbia pulcherrima* Willd. ex Klotzsch X *Euphorbia cornastra* 'Bonpridepcom', disclosed in U.S. Plant Pat. No. 21,324. In side-by-side comparisons, plants of the new *Euphorbia* differ primarily from plants of 'Bonpridepcom' in the following characteristics:

1. Plants of the new *Euphorbia* are taller, broader and more vigorous than plants of 'Bonpridepcom'.
2. Plants of the new *Euphorbia* have smaller leaves than plants of 'Bonpridepcom'.
3. Leaves of plants of the new *Euphorbia* are lanceolate in shape whereas leaves of plants of 'Bonpridepcom' are ovate in shape.
4. Plants of the new *Euphorbia* have fewer flower bracts per inflorescence than plants of 'Bonpridepcom'.

5. Plants of the new *Euphorbia* have smaller flower bracts per inflorescence than plants of 'Bonpridepcom'.
6. Plants of the new *Euphorbia* and 'Bonpridepcom' differ in flower bract color as flower bracts of plants of the new *Euphorbia* are red in color whereas flower bracts of plants of 'Bonpridepcom' are dark red purple in color.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the photographic sheet (FIG. 1) is a side perspective view of a typical flowering plant of 'BONPRI 1756' grown in a container.

Figure 2:
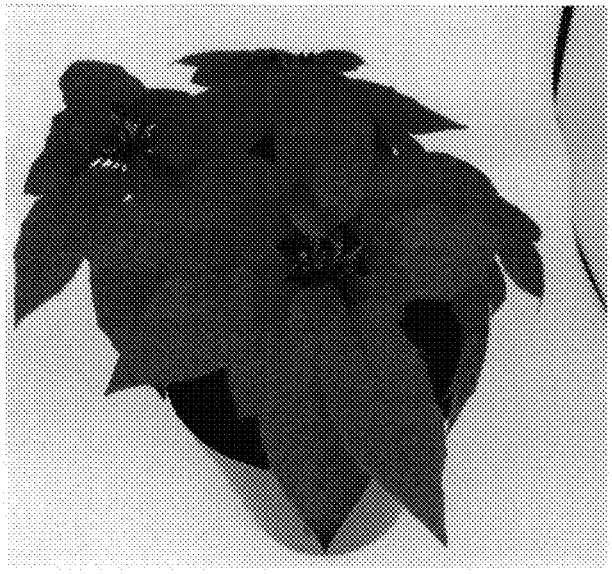

The photograph at the bottom of the photographic sheet (FIG. 2) is a top perspective view of a typical flowering plant of 'BONPRI 1756' grown in a container.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial *Euphorbia* production. During the production of the plants, day temperatures averaged 23 C and night temperatures averaged 13 C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'BONPRI 1756'.

Parentage: Naturally-occurring whole plant mutation of a proprietary selection of *Euphorbia pulcherrima* Willd. ex Klotzsch X *Euphorbia cornastra* identified as code number Eu 15-16, not patented.

Propagation:

*Type*.—Terminal vegetative cuttings.

*Time to initiate roots, summer*.—About ten days at temperatures about 20 C to 21 C.

*Time to initiate roots, winter*.—About twelve days at temperatures about 20 C to 21 C.

*Time to produce a rooted young plant, summer*.—About 24 days at temperatures about 20 C to 21 C.

*Time to produce a rooted young plant, winter*.—About 28 days at temperatures about 20 C to 21 C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 17 cm.

*Plant diameter or spread*.—About 24.2 cm.

*Lateral branch description*.—Branching habit: Freely branching habit, about five lateral branches develop per plant. Length: About 10 cm. Diameter: About 3.5 mm. Internode length: About 1.4 cm. Aspect: Mostly upright to somewhat outward. Strength: Moderately strong. Texture and luster: Smooth, glabrous; glossy. Color: Close to 146A.

*Leaf description*.—Arrangement: Alternate, simple. Length: About 6.2 cm. Width: About 3.7 cm. Shape: Lanceolate. Apex: Acute. Base: Rounded. Margin: Mostly entire, occasionally with few shallow lobes. Venation pattern: Pinnate, reticulate. Texture and luster, upper and lower surfaces: Rugose, glabrous; matte. Color: When expanding and fully developed leaves, upper surface: Close to NN137A; venation, close to 138B. When expanded and fully developed leaves, lower surface: Close to NN137C; venation, close to 138B. Petioles: Length: About 1.9 cm. Diameter: About 1.5 mm. Texture, upper and lower surfaces: Smooth, glabrous. Color, upper and lower surfaces: Close to 138B.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about five inflorescences develop per plant.

*Inflorescence diameter*.—About 16.4 cm.

*Inflorescence height*.—About 6.5 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 50 days under natural season or photoinductive conditions in Japan.

*Post-production longevity*.—Good post-production longevity; plants of the new *Euphorbia* maintain good substance and bract color for about six to eight weeks.

*Flower bracts*.—Quantity per inflorescence: About eleven. Length: About 2.3 cm. Width: About 1.5 cm. Aspect: Mostly horizontal and flat. Shape: Elliptic. Apex: Acute. Base: Attenuate. Margin: Mostly entire, occasionally with few shallow lobes. Texture and luster, upper surface: Smooth, glabrous; matte. Texture and luster, lower surface: Rough, glabrous; matte. Venation pattern: Pinnate, reticulate. Color: Transitional bracts, upper surface: Random sectors, close to 202A and 46A. Transitional bracts, lower surface: Random sectors, close to 143C and 53A. Developing bracts, upper surface: Close to N45A. Developing bracts, lower surface: Close to 53A. Fully expanded bracts, upper surface: Close to N45A; venation, close to N45C; color does not change with subsequent development. Fully expanded bracts, lower surface: Close to 45A; venation, close to 47C; color does not change with subsequent development. Flower bract petioles: Length: About 5 mm. Diameter: About 1.3 mm. Texture, upper and lower surfaces: Smooth, glabrous. Color, upper and lower surfaces: Close to 45A.

*Cyathia*.—Quantity per corymb: About 16. Diameter of cyathia cluster: About 3 cm. Height, individual cyathium: About 5.2 mm. Diameter, individual cyathium: About 3.9 mm. Shape, individual cyathium: Globose. Color: Distally, close to 46A and proximally, close to 145A. Nectaries: Quantity per cyathium: Three. Size: About 2 mm by 3.3 mm. Texture: Smooth, glabrous. Color: Close to 145A with edge, close to 46C.

*Peduncles*.—Length: About 1.6 mm. Diameter: About 1.3 mm. Texture, upper and lower surfaces: Smooth, glabrous. Aspect: Mostly upright. Color, upper and lower surfaces: Close to 144B.

*Reproductive organs*.—To date, stamen and pistil development have not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8 C to about 40 C.

It is claimed:

1. A new and distinct *Euphorbia* plant named 'BONPRI 1756' as illustrated and described.

* * * * *